(12) United States Patent
Dinkler (10) Patent No.: US 7,507,244 B2
(45) Date of Patent: Mar. 24, 2009

(54) RADIOLUCENT SKULL CLAMP WITH REMOVABLE PIN LOAD APPLICATOR

(75) Inventor: Charles E. Dinkler, Cincinnati, OH (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 808 days.

(21) Appl. No.: 10/774,769

(22) Filed: Feb. 9, 2004

(65) Prior Publication Data
US 2005/0075650 A1    Apr. 7, 2005

Related U.S. Application Data

(60) Provisional application No. 60/446,299, filed on Feb. 10, 2003.

(51) Int. Cl.
*A61B 19/00* (2006.01)
(52) U.S. Cl. ...................................................... 606/130
(58) Field of Classification Search ................. 606/130, 606/54, 56, 59; 5/622, 637, 640
See application file for complete search history.

(56) References Cited

U.S. PATENT DOCUMENTS

| | | | |
|---|---|---|---|
| 2,966,383 A * | 12/1960 | Boetcker et al. | 5/637 |
| 3,072,118 A * | 1/1963 | Standerwick et al. | 602/17 |
| 3,835,861 A * | 9/1974 | Kees et al. | 5/637 |
| 4,108,426 A | 8/1978 | Lindstroem et al. | |
| 4,360,028 A | 11/1982 | Barbier et al. | |
| 5,197,965 A * | 3/1993 | Cherry et al. | 606/54 |
| 5,269,034 A * | 12/1993 | Day et al. | 5/637 |
| 5,537,704 A * | 7/1996 | Dinkler | 5/622 |
| 6,117,143 A | 9/2000 | Hynes et al. | |
| 6,179,846 B1 | 1/2001 | McFadden | |
| 6,315,783 B1 | 11/2001 | Katz et al. | |
| 6,629,982 B2 | 10/2003 | Day et al. | |
| 7,229,451 B2 * | 6/2007 | Day et al. | 606/130 |
| 2001/0029379 A1 | 10/2001 | Grotehuis et al. | |
| 2002/0042619 A1 | 4/2002 | Dominquez et al. | |
| 2002/0151907 A1 | 10/2002 | Day et al. | |

* cited by examiner

*Primary Examiner*—Darwin P Erezo
(74) *Attorney, Agent, or Firm*—Wood, Herron & Evans (57) ABSTRACT

A skull pin assembly for use with a skull clamp includes a skull pin that is slidable into contact with a head of a patient. A pin load applicator is removably connectable to the skull pin assembly and includes a loading shaft that is able to apply a force against an inner end of the skull pin. The pin load applicator also has a biasing element operable to apply a force on the loading shaft that, in turn, transfers the force to the skull pin. A load force indicator is connected to the loading shaft and provides an indication of the force being applied by the skull pin. The pin load applicator permits the force being applied by the skull pin to be adjusted to a desired value; and thereafter, the pin load applicator is removed from the skull pin assembly without changing the desired skull pin force.

8 Claims, 6 Drawing Sheets

RADIOLUCENT SKULL CLAMP WITH REMOVABLE PIN LOAD APPLICATOR

This application claims the benefit of U.S. Provisional Application Ser. No. 60/446,299, filed Feb. 10, 2003.

FIELD OF THE INVENTION

This invention relates generally to neurosurgical apparatus and more particularly, to an improved apparatus for supporting a head of a patient.

BACKGROUND OF THE INVENTION

Generally, cranial stabilization refers to a line of compatible and interconnectable medical devices used during neurosurgery to hold the head of a patient in a fixed position relative to a surgical operating table. A typical arrangement of such products may include, for example, a base unit that connects directly to the surgical table, one or more adaptors connected to the base unit, and a skull clamp connected to an adaptor. The skull clamp often has three skull pins that engage and hold the skull of the patient.

One type of known skull clamp is designed to accommodate all sizes of heads and is comprised of two opposed clamp arms that have proximal ends slidable with respect to each other. A distal end of one clamp arm has a single skull pin, and a distal end of the other clamp arm has a rocker arm with two skull pins. Such a skull clamp and its supporting linear slide mechanism is a relatively large structure. Scanning machines require that a skull clamp and supporting structure be fully radiolucent, as small as possible and still provide flexibility and stability in supporting a patient's skull. One known approach to reducing the size of the skull clamp is to replace the two opposed sliding clamp arms with a radiolucent unitary clamp body structure.

Regardless of the general construction of the skull clamp, three skull pins are used to support the head of a patient. One skull pin is positioned to contact one side of the head; and two skull pins are positioned to contact an opposite side of the head. It is often desirable that the clamping force applied by the skull pins be distributed so that equal and opposite forces are applied to opposing sides of the head. With known designs, a force adjusting screw is threaded through the skull clamp body. A skull pin is inserted with a compression spring in an inner end of the force adjusting screw. Thus, with the skull pin contacting the head, as the force adjusting screw is tightened, the compression spring is compressed; and the skull pin applies an engagement force against the head. The magnitude of the engagement force is determined by the spring constant of the spring. A scale often extends through an outer end of the adjusting screw; and as the adjusting screw is tightened and the engagement force increases, the scale extends past the outer end of the adjusting screw an amount proportional to the engagement force. Thus, by observing the scale, the adjusting screw can be tightened to provide a desired engagement force magnitude.

While the above skull pin and force adjusting screw combination works well, it does have disadvantages. First, the compression spring within the force adjusting screw is made of metal and thus, is not radiolucent. The use of nonradiolucent materials in association with a radiolucent skull clamp body is undesirable and results in artifacts in MRI scans of the head when it is mounted in the skull clamp. Further, the manifestation of such artifacts is unpredictable and may vary from scan to scan, which makes the scanned information more difficult to interpret and use. In addition, the artifacts increase as the number of skull pins with an engagement force indicator increases. In addition, the force adjusting screw and scale extend radially outward beyond the outer perimeter of the skull clamp, which increases the envelope of space required by the skull clamp within the scanning machine.

Thus, there is a need to provide a skull pin force adjusting mechanism that does not have the disadvantages discussed above.

SUMMARY OF THE INVENTION

The present invention provides a skull pin assembly and removable pin load applicator that allows a user to easily set a desired engagement force but is fully radiolucent during an MRI scan. Further, the removable pin load applicator includes the force adjusting screw and can be removed after the engagement force is set, thereby substantially reducing the envelope of space required by the skull clamp within the scanning machine.

According to the principles of the present invention and in accordance with the described embodiments, the invention provides a skull pin assembly slidably mountable on a skull clamp. The skull pin assembly includes a skull pin that is movable to contact the head of a patient. A pin load applicator is removably connectable to the skull pin assembly and includes a loading shaft that is able to apply a force against an inner end of the skull pin. The pin load applicator also has a biasing element operable to apply a force on the loading shaft that, in turn, transfers the force to the skull pin. A load force indicator is connected to the loading shaft and provides an indication of the force being applied by the skull pin contacting the head of the patient. The pin load applicator permits the force being applied by the skull pin to be adjusted to a desired value; and thereafter, the pin load applicator can be removed from the skull pin assembly without changing the desired skull pin force.

In another embodiment, the invention includes a skull clamp having the above-described skull pin assembly and removable pin load applicator. In a further embodiment, the clamp and the skull pin assembly are made of radiolucent materials. Hence, with the metallic biasing element in the pin load applicator removed from the skull pin, there are no artifacts in a subsequent MRI scan attributable to the metallic biasing element. In a still further embodiment, the invention provides a method of using the above-described skull pin assembly and removable pin load applicator.

These and other objects and advantages of the present invention will become more readily apparent during the following detailed description taken in conjunction with the drawings herein.

DETAILED DESCRIPTION OF THE INVENTION

Figure 1:
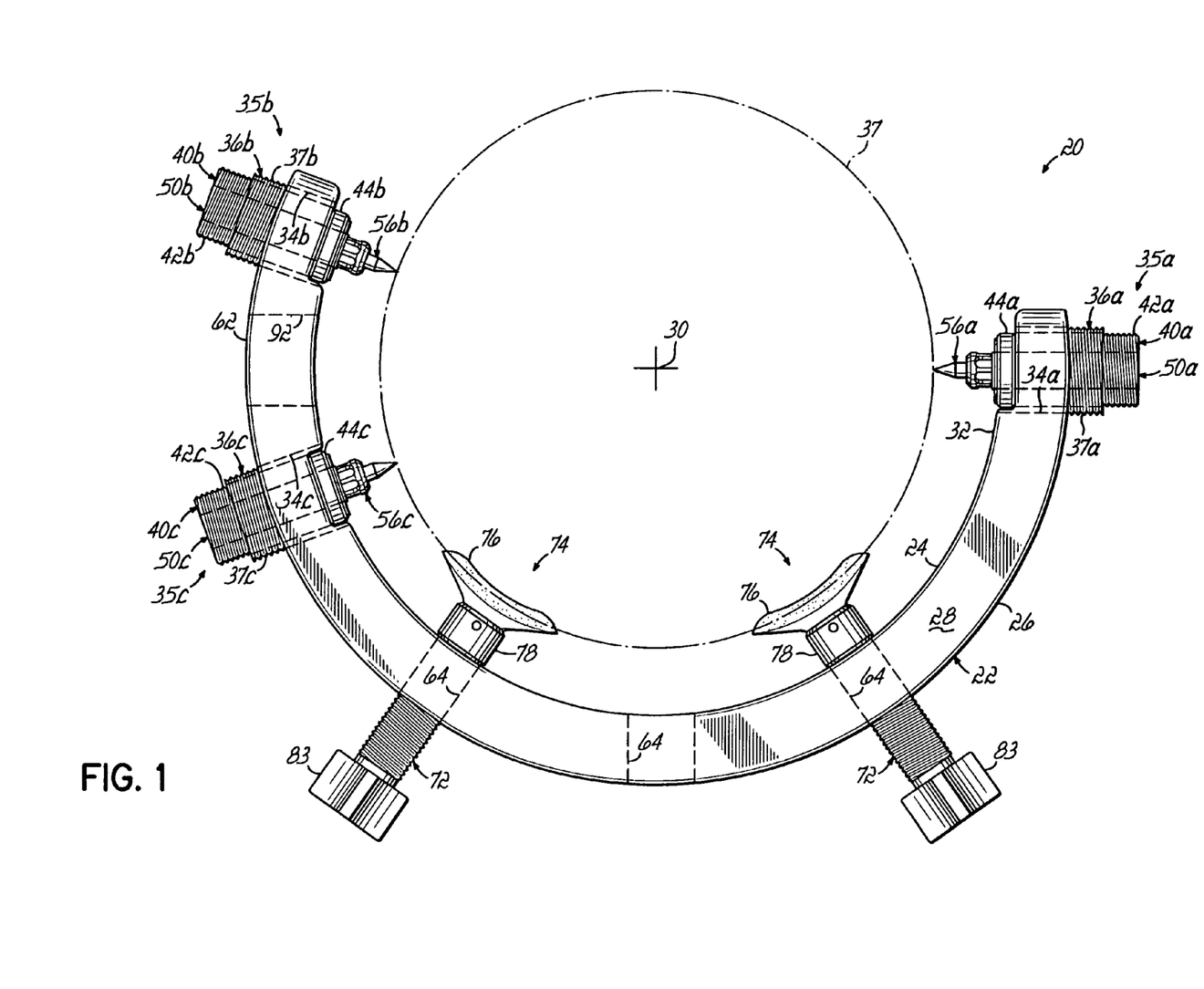
FIG. 1 is a plan view of one configuration of a radiolucent skull clamp in accordance with the principles of the present invention.

Referring to FIG. 1, a skull clamp 20 includes an arcuate, single-piece, unitary clamp body 22 that has a generally quadrilateral, for example, a rectangular, cross-sectional profile. The body 22 has an arcuate inner surface 24, an opposed arcuate outer surface 26 and opposed arcuate side surfaces 28. The body 22 is generally circular with respect to a center point 30. One end 32 of the body 22 has a generally radially directed bore 34a extending through the inner and outer surfaces 24, 26 and in which an insert 36a is rigidly mounted, for example, by an epoxy, threads or other means. A skull pin assembly 35a includes an engagement shaft 40a that is slidably mounted within the insert, and a locking nut 44a that is mounted on an inner end of the engagement shaft 40a. The skull pin assembly 35a further includes a skull pin 56a inserted in one end of a piston 50a, that, in turn, is slidably disposed within the engagement shaft 40a. The skull pin assembly 35a permits the skull pin 56a to be moved into contact with a head or skull of a patient shown schematically by the phantom line 37.

Figure 2:
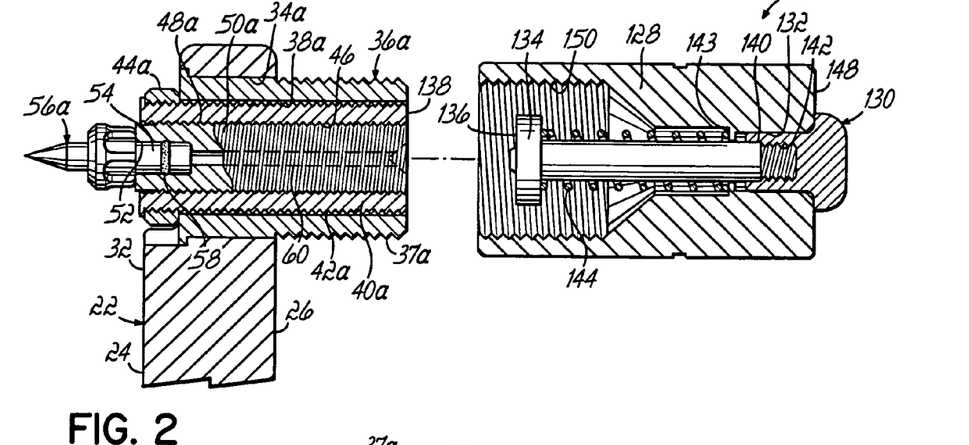
FIG. 2 is partial cross-sectional view of a skull pin assembly and a removable pin load applicator for the radiolucent skull clamp of FIG. 1.
Figure 3:
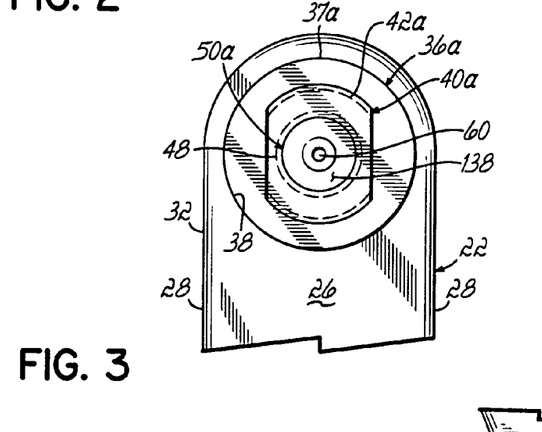
FIG. 3 is a plan view of an end of a skull pin mounting using the skull clamp of FIG. 1.

As shown in FIG. 2, the insert 36a has a smooth internal bore 38 with a noncircular cross section. An engagement shaft 40a has external threads 42a; and, as shown in FIG. 3, an external noncircular cross-sectional profile that is similar to, but slightly smaller than, the cross-sectional profile of the engagement shaft bore 38. Thus, the engagement shaft 40a is locked from rotation with respect to the insert 36a but, is able to slide linearly in a generally radial direction with respect to the clamp body 22. The noncircular cross-sectional profiles of the insert bore 38 and the exterior of the engagement shaft 40a may be of any noncircular shape that achieves the same result and also permits threads 42a to be formed on the exterior of the engagement shaft 40a, so that a locking nut 44a (FIG. 2) can be threaded over the engagement shaft threads 42a.

Referring to FIG. 2, the engagement shaft 40a has a threaded inner bore 46 that receives threads 48 of a piston 50a. The piston 50a can be threaded into either end of the engagement shaft 40a. The piston 50a has an inner end cavity 52 that is sized to receive a shank 54 of a skull pin 56a. An O-ring 58 on the skull pin shank 54 provides an interference fit with the end cavity 52 to prevent the skull pin 56a from inadvertently sliding out of the piston 50a. A central through hole 60 within the piston 50a allows air to escape from the cavity 52 when the skull pin 56a is mounted within the piston 50a.

Referring to FIG. 1, a second, opposite end 62 of the skull clamp body 22 has a respective pair of generally radially directed bores 34b and 34c extending through the inner and outer surfaces 24, 26. Skull pins 56b, 56c are mounted in the respective bores 34b, 34c in a manner substantially identical to the mounting of the skull pin 56a described above. Thus, skull pins 56b, 56c are mounted in the ends of respective pistons 50b, 50c that, in turn, are threaded into respective engagement shafts 40b, 40c. The engagement shafts 40b, 40c are slidably mounted within respective inserts 36b, 36c that are rigidly mounted within the respective bores 34b, 34c.

Figure 4:
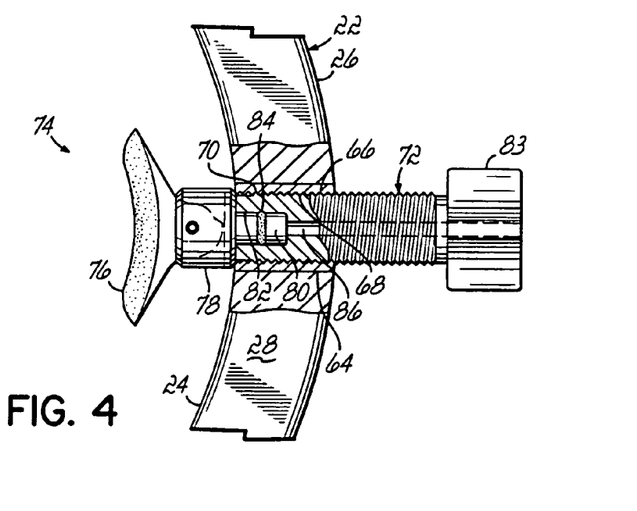
FIG. 4 is a partial cross-sectional view of a pad screw assembly used with the radiolucent skull clamp of FIG. 1.

The unitary clamp body 22 has further bores 64 that extend through the inner and outer surfaces 24, 26 in a generally radial direction with respect to the center point 30. Referring to FIG. 4, inserts 66 are rigidly fastened within the bores 64 by epoxy or other means. The outer surface of the inserts 64 may be provided with longitudinal grooves or other texturing such that the epoxy or other adhesive firmly locks the inserts 66 within the bores 64. Each of the inserts 66 has a threaded through hole 68 that is sized to receive outer threads 70 on a pad adjusting screw 72. A pad assembly 74 has a resilient pad 76 pivotally mounted to a pad support 78. A shank 80 extending from the pad support 78 is insertable in an end cavity 82 in an inner end of the pad adjusting screw 72. An O-ring 84 mounted on the shank 80 is sized to provide an interference fit within the cavity 82, thereby preventing the support pad assembly 74 from inadvertently dropping off of the pad adjusting screw 72. A central bore 86 within the pad adjusting screw permits air to escape from the cavity 82 as the shank 80 is inserted therein. Rotation of a knob 83 on an outer end of the pad adjusting screw 72 moves the pad 76 radially toward or away from the center point 30. Thus, the clamp body 22 permits up to three support pad assemblies 74 to be used to support and stabilize the skull while the skull pins 56 are properly engaged with the skull. Thereafter, the support pad assemblies 74 are backed away from contact with the skull.

Figure 5:
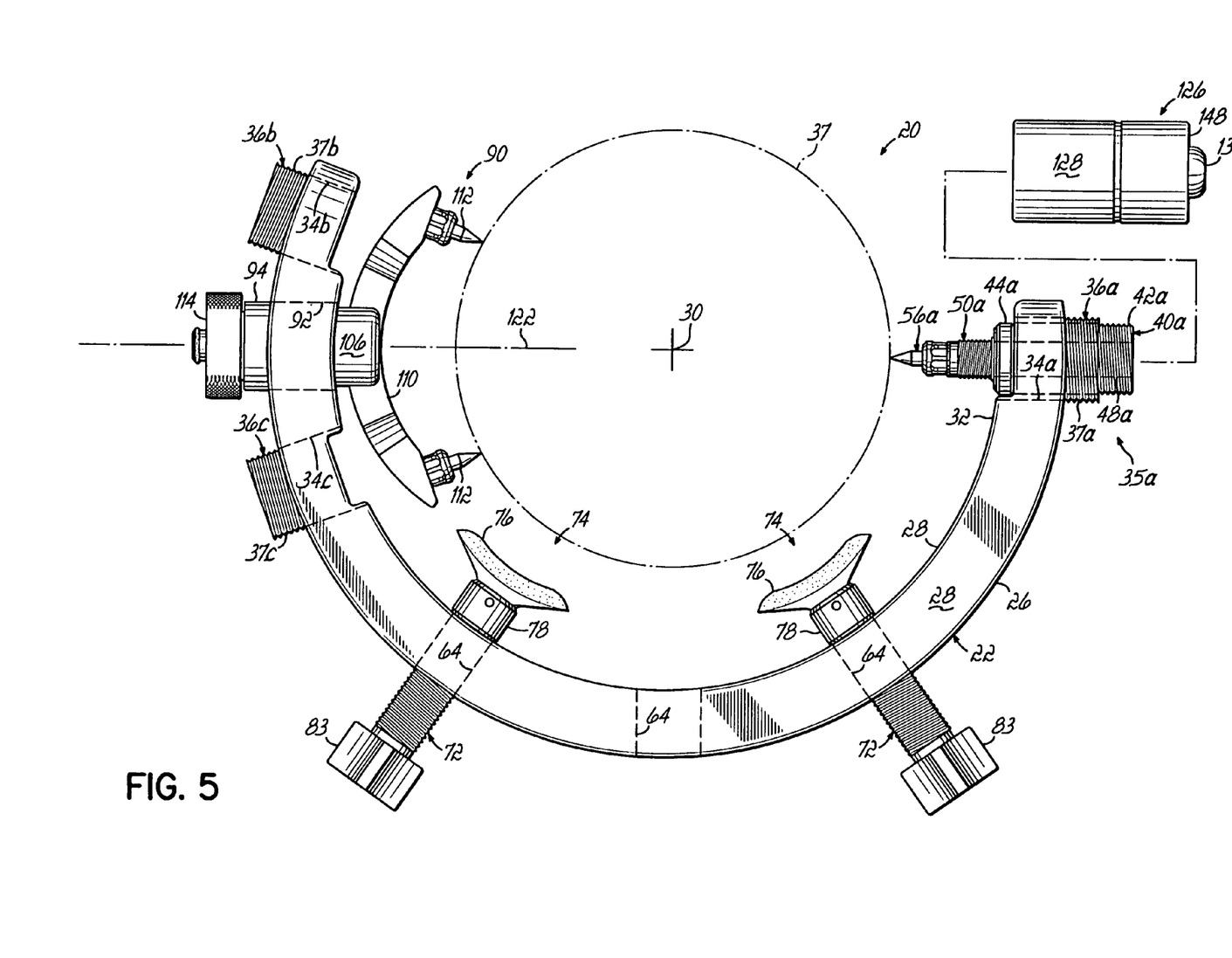
FIG. 5 is a plan view of another configuration of the radiolucent skull clamp of FIG. 1.
Figure 6:
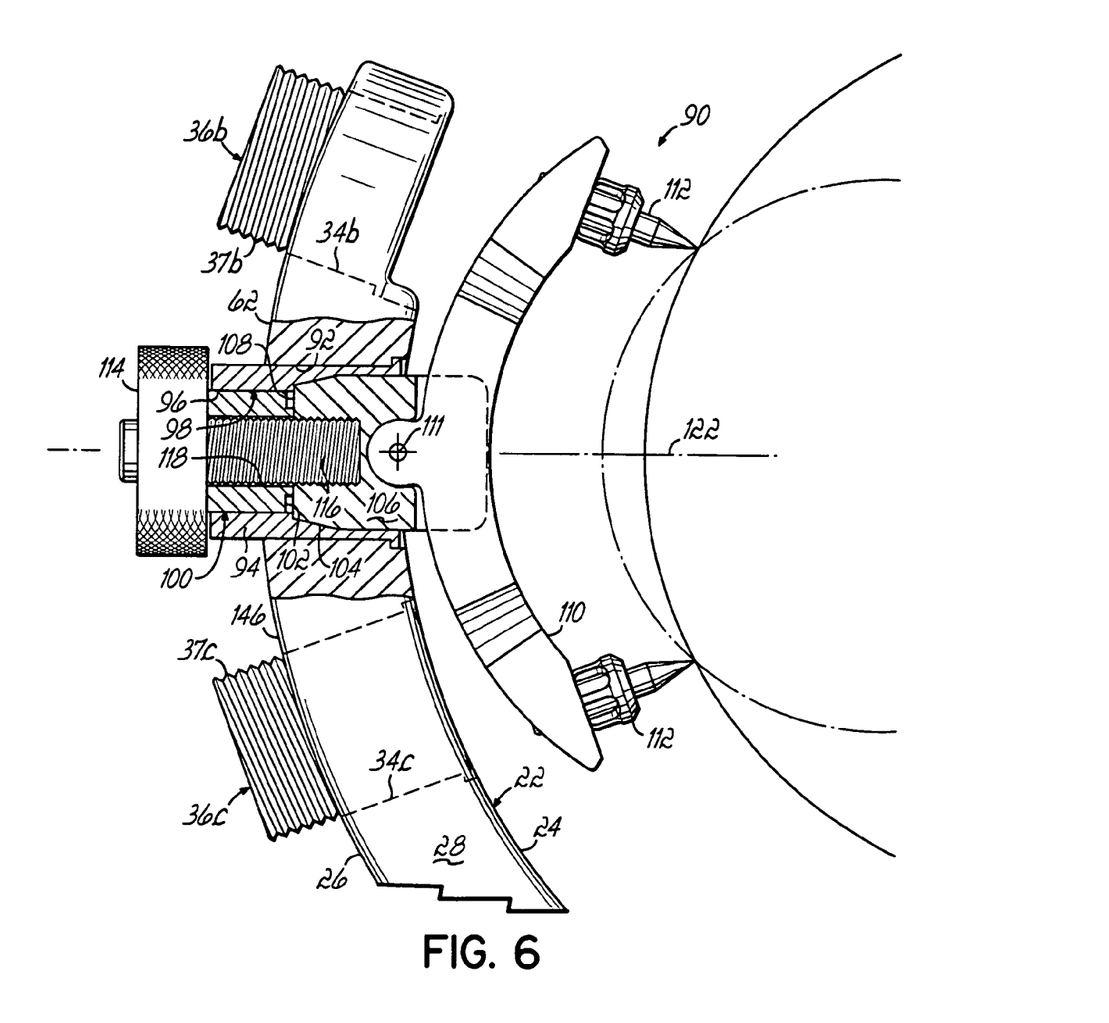
FIG. 6 is a partial cross-sectional view of a rocker arm assembly used with the radiolucent skull clamp of FIG. 1.

FIG. 5 illustrates another configuration of the skull clamp 20. First, it should be noted that the piston 50a in FIG. 5 is longer than the piston 50a shown in FIG. 1. Thus, by using pistons 50a of different lengths, a wide range of skull sizes can be accommodated. With some patients or procedures, a surgeon may prefer to utilize a rocker arm assembly 90 on an opposite end 62 of the clamp body 22 in place of the pair of skull pins 56b, 56c illustrated in FIG. 1. The pair of skull pins 56b, 56c can be removed from their respective inserts 36b, 36c by simply sliding the respective engagement shafts 40b, 40c toward the center point 30. The skull clamp body 22 has a further bore 92 that extends through the inner and outer surfaces 24, 26 at a location that is aligned generally diametrically opposite the bore 34a located in the clamp body first end 32. Referring to FIG. 6, a rocker arm insert 94 is rigidly fastened within the bore 92 by epoxy or other means. An outer end 96 of an internal bore 98 in the insert 94 has a noncircular cross-sectional profile, for example, a hexagonal shape. A swivel lock 100 has an external noncircular cross-sectional profile that is substantially similar to, but slightly smaller than, the cross-sectional profile of the bore outer end 96. Thus, when the swivel lock 100 is inserted in the bore outer end 96, it can slide longitudinally with respect to the bore 98 but is prevented from rotating with respect to the insert 94. The swivel lock 100 further has on its inner end a toothed connector 102, for example, a star burst connector comprising a ring of teeth.

The inner end 104 of the insert internal bore 98 has a flared shape that receives an inner end of a rocker arm swivel 106. A toothed connector 108 is disposed on an outer end of the rocker arm swivel 106 and located opposite the toothed connector 104 on the swivel lock 100. A rocker arm 110 is pivotally mounted in a clevis at an inner end of the rocker arm swivel 106 in a known manner to pivot with respect to a pivot axis 111, and skull pins 112 are removably mounted at ends of the rocker arm 110 in a known manner. A knob 114 is threaded on an outer end of a swivel locking screw 116. The swivel locking screw 116 extends centrally through a clearance hole 118 in the swivel lock 100 and through the toothed connector 108, and the screw 116 has an inner end that is fixed in a threaded hole in the rocker arm swivel 106. Thus, turning the knob 114 in one direction moves the knob 114 outward, that is, to the left as viewed in FIG. 6, thereby removing a clamping force from swivel lock 100 and permitting the swivel lock 100 to move slightly outward with the knob 114.

The rocker arm connector 108 then disengages from the swivel lock connector 102, which allows the rocker arm 110 to be rotated with respect to an axis of rotation 122. When the desired angular position of the rocker arm 110 is achieved, the knob 114 is rotated in an opposite direction, thereby moving it and the swivel lock 100 to the right as viewed in FIG. 6, which engages the connectors 108 and 102 and secures the rocker arm 110 at its desired angular position.

Figure 7:
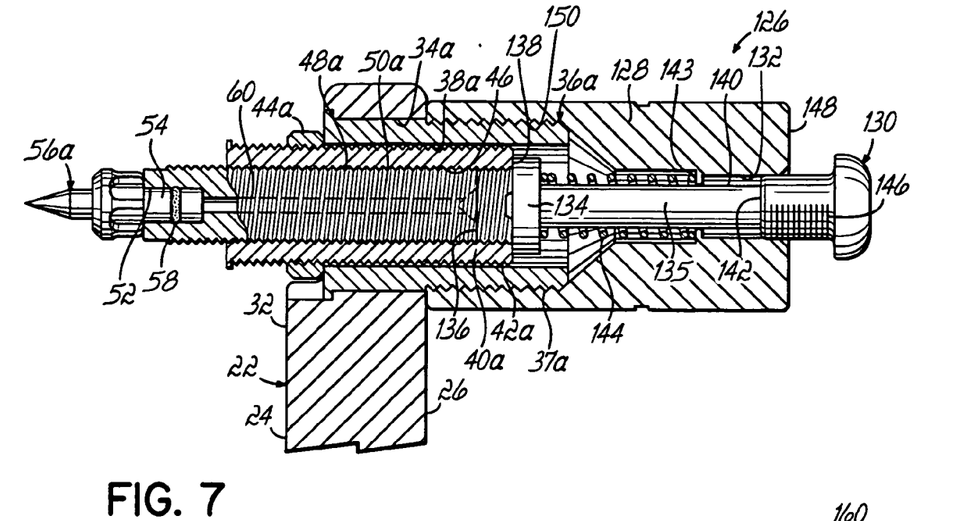
FIG. 7 is a partial cross-sectional view of the removable pin load applicator applied to a skull pin assembly of the radiolucent skull clamp of FIG. 1.

It is often desirable to be able to tighten one or more of the skull pins 56 shown in FIGS. 1 and 5 to a desired force, so that the skull is held in the skull clamp 20 with a desired clamping force. The skull clamp 20 of the present invention has the capability of controlling the clamping force applied by one or more of the skull pins 56 in all of its configurations. Referring to FIG. 7, to achieve a desired clamp force with skull pin 56a, a removable pin load applicator 126 is threaded onto the external threads 37 of the insert 34a. The removable pin load applicator 126 is comprised of a knob 128 that resiliently supports a load force indicator 130 extending through a center hole 132 of the knob 128. A plunger 134 on one end of a loading shaft 135 has an outer surface 136 that contacts an outer end 138 of the engagement shaft 40a. An opposite end 140 of the loading shaft 135 is threaded into an inner end 142 of the load force indicator 130. A biasing means 144, for example, a compression spring, extends between the plunger 134 and an internal surface 143 within the knob 128.

The knob 128 has internal threads 150 that mate with the external threads 37 on the insert 36. As the knob 128 is tightened over the insert 36, the plunger distal end 136 contacts the engagement shaft outer end 138 and pushes the engagement shaft 40a until the skull pin 56a contacts the patient's head. Continued tightening of the knob compresses the spring 144, which applies a reactive force against the engagement shaft 40a that, in turn, causes the skull pin 56a to apply the reactive force against the patient's head. Further tightening of the knob 128 increases the clamping force applied by the skull pin 56a. The force compressing the spring 144 shortens the spring 144 and causes the load force indicator 130 to move outward away from the surface 148. The outer surface of a shank portion of the load force indicator 130 contains annular markings 146 that dimensionally represent a force being applied by the skull pin 56a. When one of the force indicator rings 146 is moved to a position adjacent the surface 148, a force represented by that indicator ring is being applied by the skull pin 56a against the skull. The knob 128 is tightened until a desired force is achieved as represented by the appropriate force indicating ring 146 being positioned with respect to the surface 148. At that point, the locking nut 44 is rotated until it contacts the inner surface 24 of the clamp body 22. The knob 128 is then loosened, and the removable pin load applicator 126 is removed from the insert 36. The locking nut 44 holds the engagement shaft 40 in a position that applies the desired force against the skull via the skull pin 56a. As will be appreciated, the knob 128 can be used in the same manner to adjust the forces applied by skull pins 56b and 56c.

Figure 8:
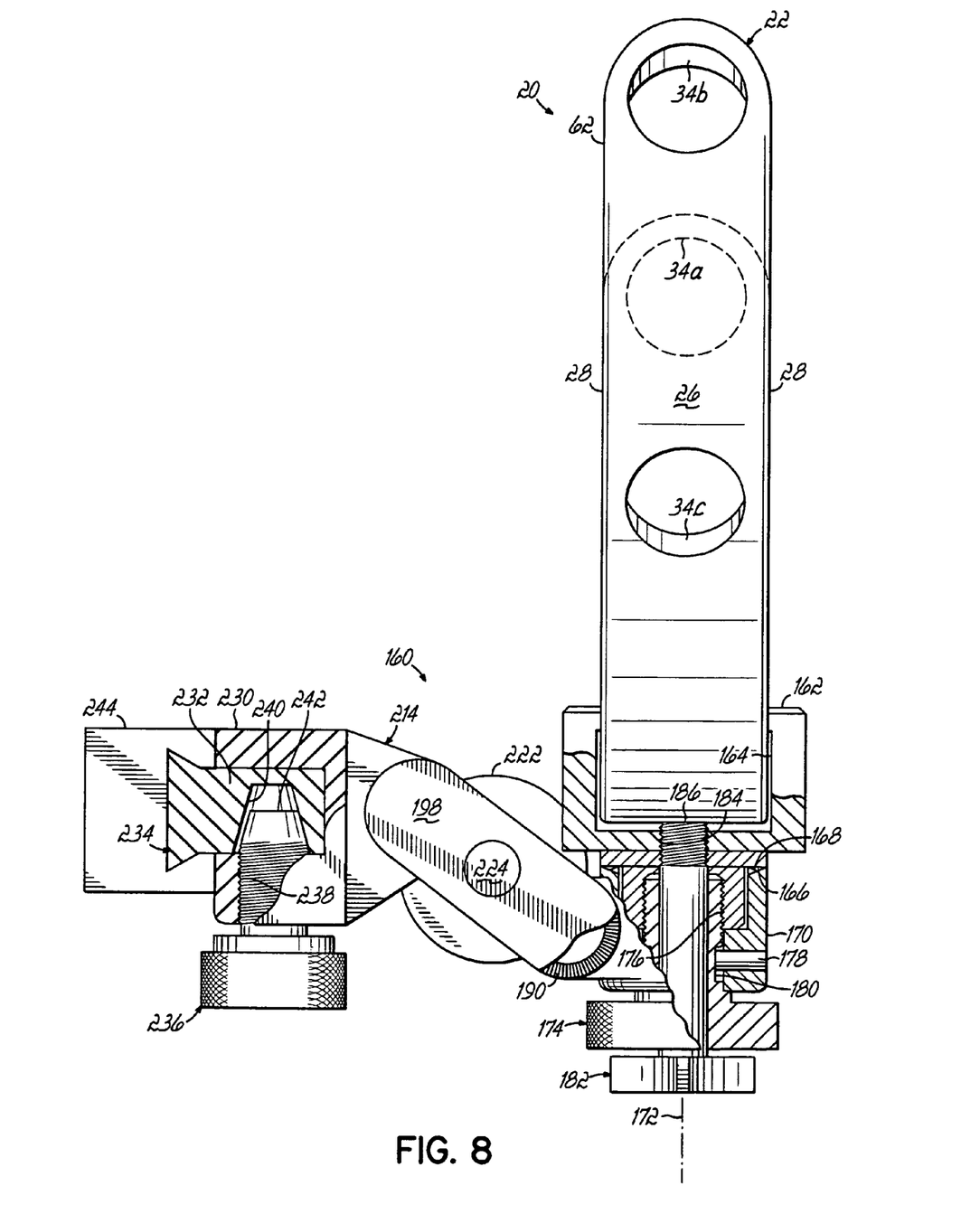
FIG. 8 is a partial cross-sectional view of a clamp support assembly for the radiolucent skull clamp of FIG. 1.
Figure 9:
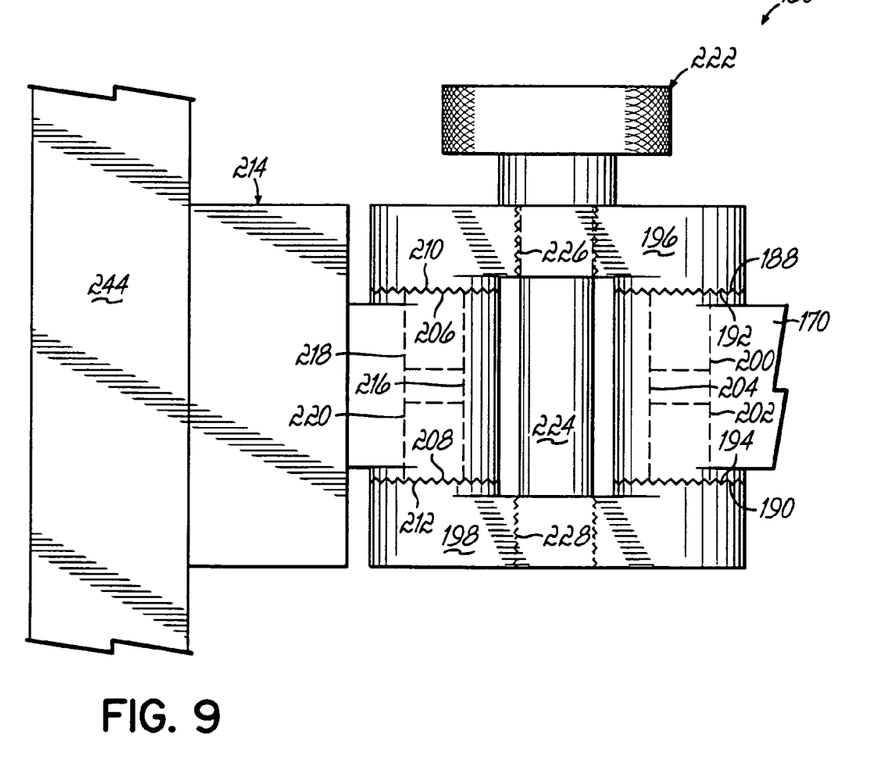
FIG. 9 is a partial cross-sectional view of a hinge plate assembly of the clamp support assembly of FIG. 5.

Referring to FIGS. 8 and 9, the skull clamp 20 is mounted to a dovetail rail 244 on a patient support by means of a skull clamp support assembly 160. A clamp support bracket 162 has an internal opening 164 with a cross-sectional shape substantially similar to, but slightly larger than, the cross-sectional profile of the clamp body 22. The clamp support bracket 162 also has a toothed connector 166 that is located adjacent to a mating toothed connector 168 on a swivel adaptor 170. Thus, the clamp support bracket 162 and clamp body 22 are able to pivot with respect to the swivel adaptor 170 and about an axis of rotation 172. A swivel locking screw 174 extends through an internal through hole in the swivel adaptor 170 and is threaded into an end cavity 176 in the lower end of the clamp support bracket 162. A pin 178 is mounted in the swivel adaptor 170 and extends into an annular groove 180 in the swivel locking screw 174. Therefore, the swivel locking screw 174 is able to rotate freely within the swivel adaptor 170 but cannot be removed therefrom. Further, rotation of the swivel locking screw 174 in one direction causes the support bracket connector 166 to separate from the swivel adaptor connector 168, thereby permitting the clamp support bracket 162 and clamp body 22 to be rotated with respect to the swivel adaptor 170. Turning the swivel locking screw in the opposite direction engages the connectors 166 and 168, thereby firmly securing the clamp support bracket 162 and clamp body 22 in a desired angular position with respect to the swivel adaptor 170.

A position locking screw 182 extends through the swivel locking screw 174 and the swivel adaptor 170 and engages a second threaded bore 184 in the lower end of the clamp support bracket 162. Rotating the position locking screw 182 in one direction forces an end face 186 of the screw against a side 26 of a clamp body 22, thereby locking the clamp body 22 within the clamp support bracket 162. Turning the position locking screw 182 in the opposite direction disengages the end surface 186 from the clamp body side 28 and permits the clamp body 22 to move freely through the opening 164 in the clamp support bracket 162.

Referring to FIG. 9, the swivel adaptor 170 has opposed toothed connectors 188, 190 that are located opposite opposed toothed connectors 192, 194 at one end of first and second hinge plates 196, 198, respectively. The hinge plates 196, 198 have respective pins 200, 202 that extend into opposite ends of a bore 204 extending through the swivel adaptor 170. Opposite ends of the hinge plates 196, 198 have respective toothed connectors 206, 208 that are located opposite toothed connectors 210, 212 of a dovetail adaptor 214. The dovetail adaptor has a through hole 216 that receives pins 218, 220 of the first and second hinge plates 196, 198, respectively. A hinge locking screw 222 has a smooth shaft 224 that extends through a threaded hole 226 of the first hinge plate 196. A distal end of the smooth shaft 224 is threaded and engages a threaded hole 228 of the second hinge plate 198. Thus, rotating the hinge locking screw 222 in the first direction disengages the opposed pairs of connectors 188, 192, 190, 194, 206, 210 and 208, 212; and the swivel adaptor 170 and the dovetail adaptor 214 are able to rotate freely with respect to each other. Rotating the hinge locking screw 222 in the opposite direction engages the opposed pairs of connectors, thereby securing the swivel adaptor 170 and the dovetail adaptor 214 at desired angular positions with respect to each other.

Referring back to FIG. 8, the dovetail adaptor 214 has a U-shaped end 230 that receives a tongue 232 of a dovetail 234. A dovetail locking screw 236 extends through a threaded hole 238 of the U-shaped end 230 and into a cavity 240 of the tongue 232. Thus, rotating the dovetail locking screw 236 in one direction displaces a distal end 242 of the dovetail locking screw 236 away from the cavity 240, thereby allowing the dovetail 234 to be removed from the dovetail adaptor 214. Turning the dovetail locking screw 236 in the opposite direction causes its distal end to contact walls of the cavity 240, thereby securing the dovetail 234 in the dovetail adaptor 214. The dovetail 234 is insertable and lockable in a dovetail rail 234 in a known manner.

In use, a patient is positioned on an operating table and/or table extension in a known manner; and the patient's head is located generally within the clamp body 22. The surgeon is then able to manipulate the skull clamp 20 and the patient's head to a desired position using various adjustments on the clamp support assembly 160 described above with respect to FIG. 8. Prior to setting the skull pin clamping force, the lengths of the pistons 50 are chosen such that the skull pins can simultaneously contact the patient's head, while a substantial portion of the pistons 50 remain threaded within the respective engagement shafts 40. Various configurations of pins 56 and the rocker arm pins 112 can be used to support the head in a wide range of positions. Further, the pads 74 are used to support and stabilize the patient's head in a desired position while the pins 56 are tightened to a desired clamping force. Thereafter, the pads 74 are moved out of contact with the patient's head.

To achieve a desired clamping force, as described with respect to FIG. 7, the removable pin load applicator 126 is first mounted on the insert 36a and used to apply the desired clamping force with the skull pin 56a. Next, the removable pin load applicator 126 is removed from the insert 36a and mounted on one of the opposed inserts, for example, the insert 36b. The knob 128 is tightened until the respective locking nut 44b just begins to move. That torque reading for the skull pin 56b is recorded, and the removable pin load applicator 126 is then mounted on the other opposed insert 36c. Again, the knob 128 is tightened until the respective locking nut 44c just begins to move. The torque reading for the skull pin 56c is read and compared to the torque reading for the skull pin 56b. If the torque readings are not substantially equal, the removable pin load applicator 126 can be used in association with one or both of the inserts 36b, 36c; and the knob 128 tightened or loosened in order to bring the forces applied by the skull pins 56 to their desired values.

The skull pin assemblies 35 are often made from commercially available radiolucent materials, for example, "DELRIN", "PEEK", "ULTEM", phenolic and/or sapphire radiolucent materials, that produce a minimum of artifacts during an MRI scanning process. When so made, the skull pin assemblies 35 with the removable pin load applicator 126 have several advantages. First, with the removable pin load applicator 126 removed, all of the skull pin assemblies 35 have the capability of applying respective desired measurable clamping forces against the skull while producing substantially the same artifacts during the MRI scanning process as radiolucent skull pins that do not have that capability. Second, as shown in FIG. 2, with the pin load applicator 126 removed, the skull pin assemblies 35 have a projection beyond the outer perimeter of the head clamp 22 that is substantially less than known skull pin and force adjusting screw combinations. Further, the pistons 50 can be made with a range of different lengths, so that the skull clamp 20 can be used with a wide range of different head sizes.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art. While the skull pin assemblies 35 and the removable pin load applicator 126 have been shown and described with respect to a single piece skull clamp body 22, as will be appreciated, the skull pin assemblies and the removable pin load applicator 126 can be used with skull clamps of other designs, for example, a skull clamp having opposed arms that are movable relative to each other. The particular design or type skull clamp shown and described herein is not to be considered a limitation on the inventions claimed.

Further, in the described embodiment, the biasing means 144 is a compression spring, but as will appreciated, in alternative embodiments, other resilient devices may be used for the biasing means 144.

In the described embodiments, the engagement shaft 40 is slidable within the insert 36; and the removable pin load applicator 126 is threaded onto the insert 36. As will be appreciated, in an alternative embodiment, the engagement shaft can be threaded into the insert; and the removable pin load applicator removably connected to the outer end of the engagement shaft, for example, by a twist and lock connection. Therefore, turning the pin load applicator rotates the engagement shaft with respect to the insert; and moves the skull pin into contact with the head of the patient. The pin load applicator is further rotated until the load indicator indicates that the skull pin is applying a desired force against the patient's head. Thereafter, the pin load applicator is removed from the engagement shaft. The threaded engagement between the engagement shaft and the insert prevents the skull pin from moving away from the patient's head; and the desired skull pin force is maintained. A locking nut may also be used to secure the engagement shaft from rotation.

Therefore, the invention in its broadest aspects is not limited to the specific details shown and described. Consequently, departures may be made from the details described herein without departing from the spirit and scope of the claims which follow.

What is claimed is:

1. An apparatus for use with a radiolucent skull clamp supporting a head of a patient comprising:
    a skull pin assembly adapted to be mounted to the skull clamp, the skull pin assembly comprising
    a skull pin adapted to be movable into contact with the head of the patient;
    an engagement shaft adapted to be slidable but not rotatable with respect to the skull clamp;
    a lock nut threaded on an inner end of the engagement shaft to limit slidable motion of the engagement shaft in a direction extending outward from the skull clamp;
    an insert adapted to be mounted to the skull clamp the insert receiving and supporting the skull pin assembly; and
    a pin load applicator adapted to be removably connectable to the skull clamp comprising
    a loading shaft in mechanical communication with the skull pin,
    a biasing element operable to apply a force on the loading shaft, the loading shaft in turn transferring the force to the skull pin contacting the head of the patient, and
    a load force indicator connected to the loading shaft and providing an indication of the force being applied by the skull pin contacting the head of the patient, the loading shaft, the biasing element and the load force indicator being contained in a unitary component that is connectable to and disconnectable from the skull clamp as a single component, the pin load applicator being movable to adjust the force applied by the skull pin contacting the head of the patient, and thereafter, the pin load applicator being removable from the skull clam without changing the force being applied by the skull pin contacting the head of the patient.

2. The apparatus of claim 1 wherein the skull pin assembly further comprises a piston supported by the engagement shaft and connected to the skull pin.

3. The apparatus of claim 2 wherein the piston is threaded within the engagement shaft and movable to change a length of the skull pin assembly.

4. The apparatus of claim 2 wherein the skull pin is supported by an inner end of the piston.

5. An apparatus for use with a radiolucent skull clamp supporting a head of a patient comprising:
- a skull pin assembly adapted to be mounted with respect to the skull clamp, the skull pin assembly comprising a skull pin adapted to be movable into contact with the head of the patient and a holder for holding the skull pin;
- a lock mounted on and adjustable relative to the holder, the lock operable to prevent movement of the skull pin away from the head of the patient;
- a pin load applicator removably connectable to the skull pin assembly and comprising a loading shaft in mechanical communication with the skull pin via the holder,
- a biasing element operable to apply a force on the loading shaft, the loading shaft in turn transferring the force via the holder to the skull pin contacting the head of the patient, and
- a load force indicator connected to the loading shaft and providing an indication of the force being applied by the skull pin contacting the head of the patient, the pin load applicator being movable to adjust the force applied by the skull pin contacting the head of the patient, so that the lock can then be adjusted relative to the holder so as to maintain said applied force, and thereafter the pin load applicator being removable from the skull pin assembly without changing said applied force being applied by the skull pin contacting the head of the patient.

6. The apparatus of claim 5 wherein said radiolucent skull clamp includes at least two such skull pin assemblies arranged on substantially opposite sides of the patient's head.

7. The apparatus of claim 5 wherein the pin load applicator connects to the skull pin assembly outboard of the skull clamp and the lock is located inboard of the skull clamp.

8. The apparatus of claim 5 wherein the holder has external threads and the lock is a nut sized to threadably engage the external threads of the holder.

* * * * *

UNITED STATES PATENT AND TRADEMARK OFFICE
CERTIFICATE OF CORRECTION

PATENT NO. : 7,507,244 B2  
APPLICATION NO. : 10/774769  
DATED : March 24, 2009  
INVENTOR(S) : Charles E. Dinkler Page 1 of 1

It is certified that error appears in the above-identified patent and that said Letters Patent is hereby corrected as shown below:

On the Title Pg. Item (74) reads "Wood, Herron & Evans LLP" and should read "Wood, Herron & Evans, L.L.P."

Col. 8, lines 40-41 Claim 1 [11] reads ". . .mounted to the skull clamp the insert receiving and supporting. . ." and should read ". . .mounted to the skull clamp, the insert receiving and supporting. . ."

Col. 8, line 58 Claim 1 [11] reads ". . .from the skull clam without changing. . ." and should read ". . .from the skull clamp without changing. . ."

Signed and Sealed this

Third Day of November, 2009

David J. Kappos
*Director of the United States Patent and Trademark Office*